United States Patent
Zeineh

(10) Patent No.: US 7,224,839 B2
(45) Date of Patent: May 29, 2007

(54) COMPRESSION PACKAGED IMAGE TRANSMISSION FOR TELEMICROSCOPY

(75) Inventor: Jack A. Zeineh, Fullerton, CA (US)

(73) Assignee: Clarient, Inc., Aliso Viejo, CA (US)

( * ) Notice: Subject to any disclaimer, the term of this patent is extended or adjusted under 35 U.S.C. 154(b) by 428 days.

(21) Appl. No.: 10/448,913

(22) Filed: May 30, 2003

(65) Prior Publication Data

US 2004/0008894 A1    Jan. 15, 2004

Related U.S. Application Data

(63) Continuation of application No. 09/323,371, filed on Jun. 1, 1999, now Pat. No. 6,606,413.

(60) Provisional application No. 60/087,523, filed on Jun. 1, 1998.

(51) Int. Cl.
  *G06K 9/36* (2006.01)
  *H04N 7/14* (2006.01)
  *G06K 9/00* (2006.01)

(52) U.S. Cl. .................... 382/232; 348/14.13

(58) Field of Classification Search ............ 382/232, 382/239, 240, 128, 151; 358/1–15; 348/14.01, 348/14.12, 14.13
See application file for complete search history.

(56) References Cited

U.S. PATENT DOCUMENTS

| | | | |
|---|---|---|---|
| 4,742,558 A | 5/1988 | Ishibashi et al. | 382/56 |
| 4,760,385 A | 7/1988 | Jansson et al. | 340/709 |
| 5,123,056 A | 6/1992 | Wilson | 382/6 |
| 5,216,596 A | 6/1993 | Weinstein | 364/413 |
| 5,252,487 A | 10/1993 | Bacus et al. | 436/63 |
| 5,257,182 A | 10/1993 | Luck et al. | 364/413 |
| 5,297,034 A | 3/1994 | Weinstein | 364/413 |
| 5,428,690 A | 6/1995 | Bacus et al. | 382/128 |
| 5,440,343 A | 8/1995 | Parulski et al. | 348/316 |
| 5,499,097 A | 3/1996 | Ortyn et al. | 356/372 |
| 5,619,032 A | 4/1997 | Kasdan | |
| 5,625,765 A | 4/1997 | Ellenby et al. | 395/135 |
| 5,655,028 A | 8/1997 | Soll et al. | 382/133 |
| 5,655,029 A | 8/1997 | Rutenberg et al. | |
| 5,790,710 A | 8/1998 | Price et al. | |
| 5,797,130 A | 8/1998 | Nelson et al. | 705/11 |

(Continued)

FOREIGN PATENT DOCUMENTS

DE    196 25 862.6 A1    6/1996

(Continued)

OTHER PUBLICATIONS

"The CAS 200™ MultiScan™ Automated Pathology Workstation," by James V. Bacus, from Becton Dickinson Cellular Imaging Systems, Elmhurst, Illinois 60126.

(Continued)

*Primary Examiner*—Yon J. Couso
(74) *Attorney, Agent, or Firm*—Fish & Richardson P.C.

(57) ABSTRACT

A system and method for visual image compression and transmission offers significant bandwidth conservation while retaining high resolution imaging capability. Videograpic images are decomposed into detail levels, and images are delivered to a remote site display at a level of detail proportional to the perception level of a viewer. Images are transformed, quantized, coded and queued for transmission in accordance with their level of image detail. Image detail layers are transmitted as an inverse function of image displacement speed and as a direct function of image magnification. Images are constructed vertically with each additional queueing layer providing additional image detail. Higher priority layers are lossy encoded, while the lowest priority layers (highest detail levels) are losslessly encoded.

24 Claims, 6 Drawing Sheets

U.S. PATENT DOCUMENTS

| | | | |
|---|---|---|---|
| 5,836,877 A | 11/1998 | Zavislan | 600/407 |
| 5,838,837 A | 11/1998 | Hirosawa et al. | 382/284 |
| 5,883,982 A | 3/1999 | Riley et al. | |
| 5,920,657 A | 7/1999 | Bender et al. | |
| 5,940,834 A | 8/1999 | Pinard et al. | 707/102 |
| 5,968,731 A | 10/1999 | Layne et al. | 435/5 |
| 6,006,191 A | 12/1999 | DiRienzo | 705/2 |
| 6,031,930 A | 2/2000 | Bacus et al. | 382/133 |
| 6,043,475 A | 3/2000 | Shimada et al. | |
| 6,075,900 A | 6/2000 | Sakazawa et al. | 382/250 |
| 6,078,681 A | 6/2000 | Silver | 382/133 |
| 6,101,265 A | 8/2000 | Bacus et al. | 382/133 |
| 6,137,915 A | 10/2000 | Chai | 382/240 |
| 6,208,374 B1 | 3/2001 | Clinch | 348/79 |
| 6,226,392 B1 | 5/2001 | Bacus et al. | 382/128 |
| 6,259,080 B1 | 7/2001 | Li et al. | |
| 6,272,235 B1 | 8/2001 | Bacus et al. | 382/133 |
| 6,396,941 B1 | 5/2002 | Bacus et al. | 382/128 |
| 6,404,906 B2 | 6/2002 | Bacus et al. | |
| 6,406,906 B1 | 6/2002 | Herbig et al. | 435/297 |
| 6,466,690 B2 | 10/2002 | Bacus et al. | |
| 6,522,774 B1 | 2/2003 | Bacus et al. | |
| 6,606,413 B1 | 8/2003 | Zeineh | |
| 6,674,881 B2 | 1/2004 | Bacus et al. | |
| 6,674,884 B2 | 1/2004 | Bacus et al. | |
| 6,711,283 B1 | 3/2004 | Soenksen | |
| 6,775,402 B2 | 8/2004 | Bacus et al. | |
| 2002/0061127 A1 | 5/2002 | Bacus et al. | 382/128 |
| 2002/0090127 A1 | 7/2002 | Wetzel et al. | 382/133 |
| 2002/0135678 A1 | 9/2002 | Bacus et al. | 348/143 |
| 2002/0149628 A1 | 10/2002 | Smith et al. | |
| 2003/0012420 A1 | 1/2003 | Verwoerd et al. | |
| 2003/0039384 A1 | 2/2003 | Bacus et al. | |
| 2003/0090127 A1 | 5/2003 | Saeki | |
| 2003/0112330 A1 | 6/2003 | Yuri et al. | |
| 2003/0123717 A1 | 7/2003 | Bacus et al. | |
| 2003/0138139 A1 | 7/2003 | Strom | |
| 2003/0184730 A1 | 10/2003 | Price | |
| 2003/0210262 A1 | 11/2003 | Gahm et al. | |
| 2003/0228038 A1 | 12/2003 | Douglass et al. | |
| 2003/0228053 A1 | 12/2003 | Li et al. | |
| 2003/0231791 A1 | 12/2003 | Torre-Bueno et al. | |
| 2004/0004614 A1 | 1/2004 | Bacus et al. | |
| 2004/0136582 A1 | 7/2004 | Bacus et al. | |
| 2004/0141637 A1 | 7/2004 | Bacus et al. | |
| 2004/0236773 A1 | 11/2004 | Bacus et al. | |

FOREIGN PATENT DOCUMENTS

| | | |
|---|---|---|
| DE | 197 07 026 A1 | 2/1997 |
| JP | 02272413 | 11/1990 |
| JP | 09037232 | 2/1997 |
| JP | 09051498 | 2/1997 |
| JP | 09117417 | 5/1997 |
| JP | 10186238 | 7/1998 |
| JP | 10224783 | 8/1998 |
| JP | 10274741 | 10/1998 |
| JP | 11009556 | 1/1999 |
| WO | WO 98/0199 | 1/1998 |
| WO | WO 98/08342 | 2/1998 |
| WO | WO 98/39728 | 9/1998 |
| WO | WO 98/41022 | 9/1998 |
| WO | WO 99/13360 | 3/1999 |
| WO | WO 99/13400 | 3/1999 |
| WO | WO 99/14882 | 3/1999 |
| WO | WO 02/056084 | 1/2002 |
| WO | WO 02/056256 | 1/2002 |
| WO | WO 02/50759 | 6/2002 |

OTHER PUBLICATIONS

"Telepathology and the Networking of Pathology Diagnostic Services," by Ronald S. Weinstein, M.D., et al., published in Arch. Pathol. Lab. Med., vol. 111, Jul. 1987.

"Aspects of Standardization in Telepathology," by K. Kayser, P. Schwarzmann, Department of Pathology, Thoraxklinik, Heidelberg, Institute of Applied Electronics, University of Stuttgart, Germany, 1992.

"The Distributed Laboratory," SIGraph '92 Showcase, vol. 35, No. 6, Communications of the ACM, Jun. 1992.

"Progress in Telepathology," by K. Kayser, Department of Pathology Thoraxklinik, D-6900 Heidelberg, Germany, 1993.

"Telemicroscopy," by G. Y. Fan, P. J. Mercurio, S. J. Young, and M. H. Ellisman, Ultramicroscopy, 1993.

"Telepathology With an Integrated Services Digital Network—A New Tool for Image Transfer in Surgical Pathology: A Preliminary Report," by Martin Oberholzer, M.D., et al., Department of Pathology and the Computer Centre and Institute of Informatics, University of Basel, Basel, Switzerland, 1993.

"Telepathology Is Available for Transplantation-Pathology: Experience in Japan Using an Integrated, Low-cost, and High-Quality System," by Hisas Ito, et al., from Modern Pathology, vol. 7, No. 7, p. 801, 1994.

"Compendium on the Computerized Cytology and Histology Laboratory," by George L. Wied, et al., Tutorials of Cytology, Chicago, Illinois U.S.A, 1994.

"Telepathology," by Shigeru Arai, M.D., Department of Pathology, Yamagata University School of Medicine, Yamagata 990-23, Japan, 1995.

"Telepathology: Frozen Section Diagnosis at a Distance," by M. Oberholzer, et al., Springer-Verlag, 1995.

"Telepathology: Expert Center Cooperation in the Field of Anatomic Pathology," by James O'D. McGee, et al. The Journal of Pathology, vol. 175, p. 152A, 1995.

"Teleradiology/Telepathology Requirements and Implementation," Seong K. Mun, et al., Journal of Medical Systems, vol. 19, No. 2, pp. 153-164, 1995.

"Expert Consultation by Use of Telepathology—The Heidelberg Experiences," by Klaus Kayser, et al., published in Analytical Cellular Pathology, No. 9, pp. 53-60, 1995.

"Quick Return Service of the Surgical Pathology," by Seiichi Tamai, M.D., 43, pp. 1017-1023, 1995.

"The Validity of Intraoperative Frozen Section Diagnosis Based on Video-microscopy (Telepathology)," published in General & Diagnostic Pathology, 141, pp. 105-110, 1995.

"Telepathology: A Tool to Aid in Diagnosis and Quality Assurance in Cervicovaginal Cytology," by C. Marsan, et al., published in Cytopathology, 6, pp. 339-342, 1995.

"Apport de l'infomratique et de la téléphathologie en anatomocytopathologie cancérologique," by Ed Martin, et al., published in Bull Cancer, 82, Supp. 5, 565s-568s, 1995.

"Télémédecine Et Responsabilitié Médicale," by F.A. Allaert, et al., published in Arch. Anat. Cytol. Path., 43, n 4, pp. 200-205, 1995.

"A Contribution to the Quantitative Analysis of Transmitted Images," by A. D ubur, et al., published in Arch. Anat. Cytol. Path., 43, n 4, pp. 268-270, 1995.

"Telepathology: Clinical Assessment of an International Network," by A. Bhattacharyya, et al., International Academy of Pathology, 84th Annual Meeting, Toronto Sheraton Center, Mar. 11-17, 1995, published in Modern Pathology, vol. 8, No. 1, p. 162A, Jan. 1995.

Evaluation of High Resolution Diagnostic Images After Wavelet Based Image Compression, by L.A. Langford, et al., published in The FASEB Journal, vol. 9, No. 4, p. A1067, Mar. 10, 1995.

Microscopy ListServer Archives, E-mail from Bram Koster, printed from http://www.msa.microscopy.com/MicroscopyListserver/MicroscopyArchives.html, Jun. 22, 1995.

"Remote Microscope for Inspection of Integrated Circuits," by James T. Kao, Massachusetts Institute of Technology, Sep. 1995.

"Telemedicine: Delivering Medical Expertise Across the State and Around the World," by Henry A. Swett, M.D., et al., published in Connecticut Medicine, vol. 59, No., 10, Oct. 1995.

"Evaluation of a Telepathology System Between Boston (USA) and Dijon (France): Glass Slides Versus Telediagnostic TV-Monitor," by F.A. Allaert, et al., Nineteenth Annual Symposium on Computer Applications in Medical Care, Oct. 28-Nov. 1, 1995.

"Fastest is Always Best and Other PACS Fallacies," by Mike Cannavo, published in Health Management Technology, Nov. 1995.

"A New Paradigm—Multi-User Scanning Electron Microscopy," by L.S. Chumbley, et al., JOM, 47(9), pp. 13-17, 1995, copy printed on Jun. 14, 2003, from Web site http://www.tims.org/pubs/journals/JOM/9509/Chumbley-9509.html.

"Automated Digital Image Mosaicing for Telemicroscopy," by Steven T. Peltier, University of California, San Diego, 1996.

"Factor Influencing Distant Tele-evaluation in Cytology, Pathology, Conventional Radiology and Mammography," by Olga Ferrer Roca, et al., published in Analytical Cellular Pathology, 10, pp. 13-23, 1996.

"Quantitative DNA Ploidy Analysis of Breast Carcinoma: A Study of the Effects of Joint Photographer Expert Group (JPEG) Compression on DNA Ploidy Images," by Laura A. Phillips, M.L.T., et al., Diagnostic Cytopathology, vol. 15, No. 3, pp. 231-236, 1996.

"Stratégie d'utilisation du télediagnostic et de la banque d'images," by G. Flandrin, Ann. Pathol., 16, n 3, p. 155-158, 1996.

"Telepathology Through the Internet," by V. Della Mea, et al., published in the Journal of Telemedicine and Telecare, vol. 2, Supp. 1996.

"Frozen-section Services by Telepathology: Experience of 100 Cases in the San-in District, Japan," by Hironobu Adachi, et al., published in Pathology International, 46, pp. 436-441, 1996.

"Evaluating Image for 'International Consortium for Internet Telepatholgy Project (ICIT),'"by Y. Yagi, et al., published in Blackwell Scientific Publication for Pathology International, 46 (Suppl. 1), Japanese Society of Pathology, 1996.

"Telemedizin," by K. Kayser, published in Wien Klin Wochenschr, 108/17, pp. 532-540, 1996.

"Image Analysis (IA) of Skin Specimens: The Application of Telepathology (TP) to Frozen Section Evaluation," by L.B. Jacobs, et al., published in Modern Pathology, vol. 9, No. 1, p. 172A, Jan. 1996.

"Diagnostic Accuracy of An Interactive Telepathology System," by R.O. Rainer, et al., published in Modern Pathology, vol. 9, No. 1, Jan. 1996.

"Telepathology: Utility, Diagnostic Accuracy and Interobserver Variability on a Difficult Case Consultation Service," by S.S. Raab, et al., published in Modern Pathology, vol. 9, No. 1, p. 166A, Jan. 1996.

"Telepathology Diagnoses of Prostate Needle Biopsies," by M.H. Weinstein, et al., published in Modern Pathology, vol. 9, No. 1, p. 85A Jan. 1996.

"Static Image Telepathology in Perspective," by Ronald S. Weinstein, M.D., published in Human Pathology, vol. 27, No. 2, pp. 99-101, Feb. 1996.

"Telepathology Diagnosis by Means of Digital Still Images: An International Validation Study," by David S. Weinberg, M.D., et al., Human Pathology, vol. 27, No. 2, pp. 111-118, Feb. 1996.

"Implementing a Collaboratory for Microscopic Digital Anatomy," by Stephen J. Young, et al., published in The International Journal of Supercomputer Applications and High Performance Computing, vol. 10, No. 2/3, pp. 170-181, Summer/Fall 1996.

"Proceedings of the International Conference of Telepathology," Double Tree Hotel, Rockville, Maryland, USA, Dec. 5-7, 1996.

"WebSlide Browser, A Thin Client Browser for Internet/Intranet Microscopy," three-page Web site printout from http://web.archive.org/web/19900429034329/http://www.mcs.net/~bacuslab/WebSlide.html, Copyright © 1998 Bacus Laboratories, Inc.

Search Report from the European Patent Office, re "Remote Controlled Examination of Pathology Specimens," Jul. 18, 2003addressed to Jeffer, Mangels, Butler & Marmaro, LLP, Attn. Mr. David J. Meyer, Jul. 22, 1999.

CMDA GridManager, Computer Printout, printed May 30, 2002.

"ORNL's Telepresence Connects Researcher with Remote Microscope," Press Release, from http://www.ornl.gov/Press_Releases/archive/mr19960627-01.html, printed Jun. 14, 2002.

"Apollo Software Inc.," Advertising Material, printed Jun. 24, 2002.

"Telemedicine Project in the Azores Islands," by L. Concalves and C. Cunha, Arch. Anat. Cytol. Path., pp. 285-287, 1995.

"Bruk av telekommunikasjon i patologisk-anatomisk service," Klinikk og forskning, Tidsskr Nor Lageforen nr., 1, 111:17-19, 1991.

Health Care Financing Administration (HCFA) and Reimbursement in Telemedicine, by Helen L. Smits and Abby Baum, Journal of Medical Systems, vol. 19, No. 2, 1995.

"Telepathology. Long-Distance Diagnosis," by Ronald S. Wenstein, M.D., Kenneth J. Bloom, M.D., and L. Susan Rozek, R.N., A.J.C.P., Apr. (Supp. 1), 1999.

Search results: "Use of Telecommunications in Pathology and Anatomy Services," by Eide TJ, Nordrum I, Engum B, Rinde E., Patologisk-anatomisk avdeling, Tromso.

"Quantitative DNA Analysis: A Comparison of Conventional DNA Ploidy Analysis and Teleploidy," by K.L. Phillips, L. Anderson, Th. Gahm, L.B. Needham, M.L. Goldman, B.E. Wray, T.F. Macri, Arch. Anat. Cytol. Path., pp. 288-295, 1995.

"The Design and Use of A Computer-Based Digital Image Acquisition, Management, and Communications System for Conferencing in Pathology," by B.E. Wray and M. Lai-Goldman, pp. 271-274, Arch. Anat. Cytol. Path, vol. 43, No. 4, 1995.

"Multimedic System for Telepathology and Interdisciplinary Councils Between Doctors and Various Hospitals," by H.A. Richter, M. Danaei, N. Maurin, and C. Mittermayer, pp. 296-299, Arch. Anat. Cytol. Path., vol. 43, No. 4, 1995.

"Concept of Telepathology in Croatia," Z. Danilovkc, A. Dzubur, and S. Seiwerth, pp. 282-284, Arch. Anat. Cytol. Path., vol. 43, No. 4, 1995.

"Pathology Consultation Services Via The Arizona-International Telemedicine Network," by R.S. Weinstein, A. Bhattacharyya, Y.P. Yu, J.R. Davis, J.M. Byers, A. R. Graham, R. Martinez, pp. 219-226, Arch. Anat. Cytol. Path., vol. 43, No. 4, 1995.

"Fiabilite Du Diagnostic Anatomo-Pathologique Par Transmission D'Images Statiques," by A. Vieillefornd, F. Staroz, M. Fabre, P. Bedossa, V. Martin-Pop, E. Martin, C. Got, and B. Franc, pp. 246-250, Arch. Anat. Cytol. Path., vol. 43, No. 4, 1995.

"Experience With Distant Pathology Demonstrations for Clinicians in Hospitals Without Local Pathologiest Through the Swedish Telepathology Work Station," by B.R. G. Boeryd, pp. 266-267, Arch. Anat. Cytol. Path., vol. 43, No. 4, 1995.

"Télécytoconsultation: Application Du Systeme Transpath à la Pathologie Cervico-Vaginale," by M.C. Vacher-Lavenue and C. Marsan, pp. 262-265, Arch. Anat. Cytol. Path., vol. 43, No. 4, 1995.

"Aspects of Telepathology in Routinary Diagnostic Work With Specific Emphasis on ISDN," by K. Jayser, P. Fritz and M. Drlicek, pp. 216-218, Arch. Anat. Cytol. Path., vol. 43, No. 4, 1995.

"Telemicroscopy Stations For Telepathology Based on Broadband and ISDN Connections," by P. Schwarzmann, J. Schmid, C. Schnorr, G. Strble, and S. Witte, pp. 209-215, Arch. Anat. Cytol. Path., vol. 43, No. 4, 1995.

"Telepathology in Europe, It's Practical Use," by K. Kayser, pp. 196-199, Arch. Anat. Cytol. Path., vol. 43, No. 4, 1995.

"Remote Frozen Section Service in Norway," by I. Nordrum and T.J. Eide, pp. 253-256, Arch. Anat. Cytol. Path., vol. 43, No. 4, 1995.

"Adult Multiocular Cyst and Nephroblastomatosis," by O. Ferrer-Roca, A. Sanroman, and J. H. Rodriguez, pp. 234-236, Journal of Telemedicine and Telecare, 1995.

"A Pilot Study of the Physician Acceptance of Tele-oncology," by Ace Allen, Jeanne Hayes, Raj Sadasivan, Stephen K. Williamson, and Connie Wittman, pp. 34-37, Journal of Telemedicine and Telecare, 1995.

"Computers in Radiology, Making Global Telemedicine Practical and Affordable: Demonstrtions from the MIddle East," by Mark A. Goldberg, Hassan S. Sharif, Daniel L. Rosenthal, Stephen Black-Schaffer, Thomas J. Flotte, Robert B. Colvin, and James H. Thrall, pp. 1495-1500, AJR, 1994.

"Current Status of Telepathology," by Tor J. Eide and Ivar Nordrum, pp. 881-890, APMIS 102, 1994.

Telepathology With an Integrated Services Digital Network—A New Tool for Image Transfer in Surgical Pathology: A Preliminary Report, by Martin Oberholzer, M.D., Hans-Rudolf Fischer, et al., pp. 1078-1085, Human Pathology, vol. 24, No. 10, Oct. 1993.

"Use of Remote Video Microscopy (Telepathology) as an Adjunct to Neurosurgical Frozen Section Consultation," by R. L. Becker, Jr., M.D., Ph.D., et al, pp. 909-911, Human Pathology, vol. 24, No. 8, Aug. 1993.

"Legal Aspects of Telepathology," by M. Schiffer, pp. 393-394, Zentralbl. Pathol. 138, 1992.

"Aspects of Standardization in Telepathology," by K. Kayser and P. Schwarzmann, pp. 389-392, Zentralbl. Pathol. 138, 1992.

"Telepathology in Sweden, A National Study Including all Histopathology and Cytology Laboratories," pp. 429-430, Zentralbl. Pathol. 138, 1992.

"Human Performance Studies of the Video Microscopy Component of a Dynamic Telepathology System," by Ronald S. Weinstein, Kennth J. Bloom, Elizabeth A. Krupinski, and L. Susan Rozek, pp. 399-401, Zentralbl. Pathol. 138, 1992.

"Telepathology—Visual Telecommunication in Pathology, An Introduction," pp. 381-382, Zentralbl. Pathol. 138, 1992.

"Experence and Present Status of Telepathology in the National Cancer Center Hospital, Tokyo," by Yukio Shimosato, Yukako Yagi, et al, pp. 413-417, Zentralbl. Pathol. 138, 1992.

"Telepathology: A New Tool of Pathology? Presentation of a French National Network," by Etienne Martin, Pierre Dusserre, et al., pp. 419-423, Zentralbl. Pathol. 138, 1992.

"Telepathology in Greece, Experience of the Metaxas Cancer Institute," by G. Miagulis, E. Protopapa, et al., pp. 425-428, Zentralbl. Pathol. 138, 1992.

"Telemicroscopy, Design Considerations for a Key Tool in Telepathology," by P. Schwarzmann, pp. 183-187, Zentralbl. Pathol. 138, 1992.

"Remote Frozen Section Service: A Telepathology Project in Northern Norway," by Ivar Nordrum, M.D., Bjorn Engum, M.S., et al, pp. 514-518, Human Pathology, vol. 22, No. 6, Jun. 1991.

"Telepathology Comes of Age in Norway," by Ronald S. Weinstein, M.D., Human Pathology, vol. 22, No. 6, Jun. 1991.

COMPRESSION PACKAGED IMAGE TRANSMISSION FOR TELEMICROSCOPY

CROSS-REFERENCE TO RELATED APPLICATIONS

This is a continuation of application Ser. No. 09/323,371, filed Jun. 1, 1999, now U.S. Pat. No. 6,606,413 which claims benefit of U.S. Provisional Application No. 60/087,523, filed Jun. 1, 1998.

FIELD OF THE INVENTION

The present invention relates generally to the field of remote operation and viewing of a videographic imaging system and, more particularly, to the acquisition and transmission of images useful in the field of telemedicine to effect remote site diagnostic and consultation procedures.

BACKGROUND OF THE INVENTION

The digital revolution has intruded in almost every sphere of modern electronic communications and has given rise to applications and abilities that were not even considered prior to the introduction of the small platform computer system in the late 1960's and its subsequent development through the 70's, 80's and 90's. Although totally pervasive in every aspect of society and sector of the economy, the digital revolution has had a significant impact in the field of electronic communication and, most particularly, to that area relating to the capture, transmission and faithful reproduction of audiographic and videographic data. No one field has benefitted more from the capabilities generated by the digital revolution than that of telemedicine.

Functionally, telemedicine allows a physician to have a remote site capability by means of which they are able to direct procedures, make diagnosis, and generally engage in the practice of certain forms of medicine without the need to be physically present in the operating theater or the examination room in order to effect a practically real-time interaction. In the field of pathology, specifically, telemedicine (telepathology to be more precise) allows the investigating pathologist to be separated from the local origin of tissue to be investigated and, ideally, still be able to make an effective investigation of a tissue sample in order to render a diagnostic opinion.

The current trend in telemedicine in general, and telepathology in particular, gives rise to some very interesting implications for the quality of healthcare services available to the public at large. Telepathology particularly allows a surgeon about to perform an invasive surgical procedure, to select a particular specialist without regard to that specialist's location. Selection of pathology services need only be made, therefore, by determining those most suited, or experienced, in dealing with the particular organ system under consideration. In the daily routine of a large hospital, such service flexibility becomes highly relevant when the diverse character of the procedures carried out as such hospitals is considered. Likewise, small to medium sized hospitals, which may not be able to support a large pathology staff incorporating the many subspecialties required for full coverage, are able to avail themselves of the same quality of pathology services that one might find in a major urban hospital. Clearly, the benefits of telemedicine, particularly telepathology, would be most greatly felt by small to medium sized hospitals in remote areas of the country where the size and quality of specialty medical staff is necessarily limited to due to geographical isolation.

The enabling tool for providing telepathology services is a telemicroscopy system connected to a bi-directional telecommunications network which is pervasive enough to allow the necessary equipment to be set up and operated virtually anywhere. Conventional forms of telemicroscopy equipment are generally well known in the art and suitably comprise a remote controlled microscope system where microscope images are acquired with a conventional video camera and transmitted, for display, to a control system. Remote operation of the microscope system and remote display of transmitted images can be realistically performed using a variety of communications technologies. However, in order to ensure a general availability of a developing telepathology network, interconnectivity is most realistic in the context of narrow band or broadband landline connections. Narrow band systems (like PSTN and ISDN) generally guarantee worldwide availability for very low costs, but at the price of bandwidth and/or channel capacity. Broadband systems (like ATM) allow enhanced channel capacity but still suffer from a lack of sufficient bandwidth to allow video transmissions at anything approximating real-time. Because of these limitations, conventional telemicroscopy systems have had to make certain compromises between channel capacity and image quality. The higher the quality of the transmitted image, the longer the time it takes to complete a transmission. Conversely, when transmission speed is an overriding concern, image quality necessarily suffers.

With a limited bandwidth available on PSTN (Public Switched Telephone Network) and ISDN (Integrated Services Digital Network), the only means available to increase transmission speed is to reduce the average number of transmitted bits per image, i.e., compress the digital image data developed by video camera. Before telepathology services become truly viable, image transmission must operate at bit rates of only a few hundred kilobits or a few megabits per second, which can only be achieved through rather large compression of the data.

Most sensory signals contain a substantial amount of redundant or superfluous information. For example, a conventional video camera, that captures approximately 30 frames per second from a stationary image, produces very similar frames, one after the other. Compression techniques attempt to remove the superfluous information from repetitive frames, such that a single frame can be represented by a reduced amount of finite data, or in the case of time varying images, by a lower data rate. It is well known in the art that digitized video signals comprise a significant amount of statistical redundancy, i.e., samples are similar to each other such that one sample can be predicted fairly accurately from another. By removing the predictable or similarity component from a stream of samples, the video data rate can be reduced. Such statistical redundancy is able to be removed without perturbing the remaining information. That is, the original uncompressed data is able to be recovered almost exactly by various inverse operations. The algorithms used in a compression system depend on the available bandwidth, the features required by the application, and the affordability of the hardware required for implementation of the compression algorithm on both the encoding and decoding side.

BRIEF DESCRIPTION OF THE DRAWINGS

The particular features, aspects and advantages of the present invention will be more fully understood when considered with respect to the following detailed description and accompanying drawings wherein.

DETAILED DESCRIPTION OF THE INVENTION

Figure 1:
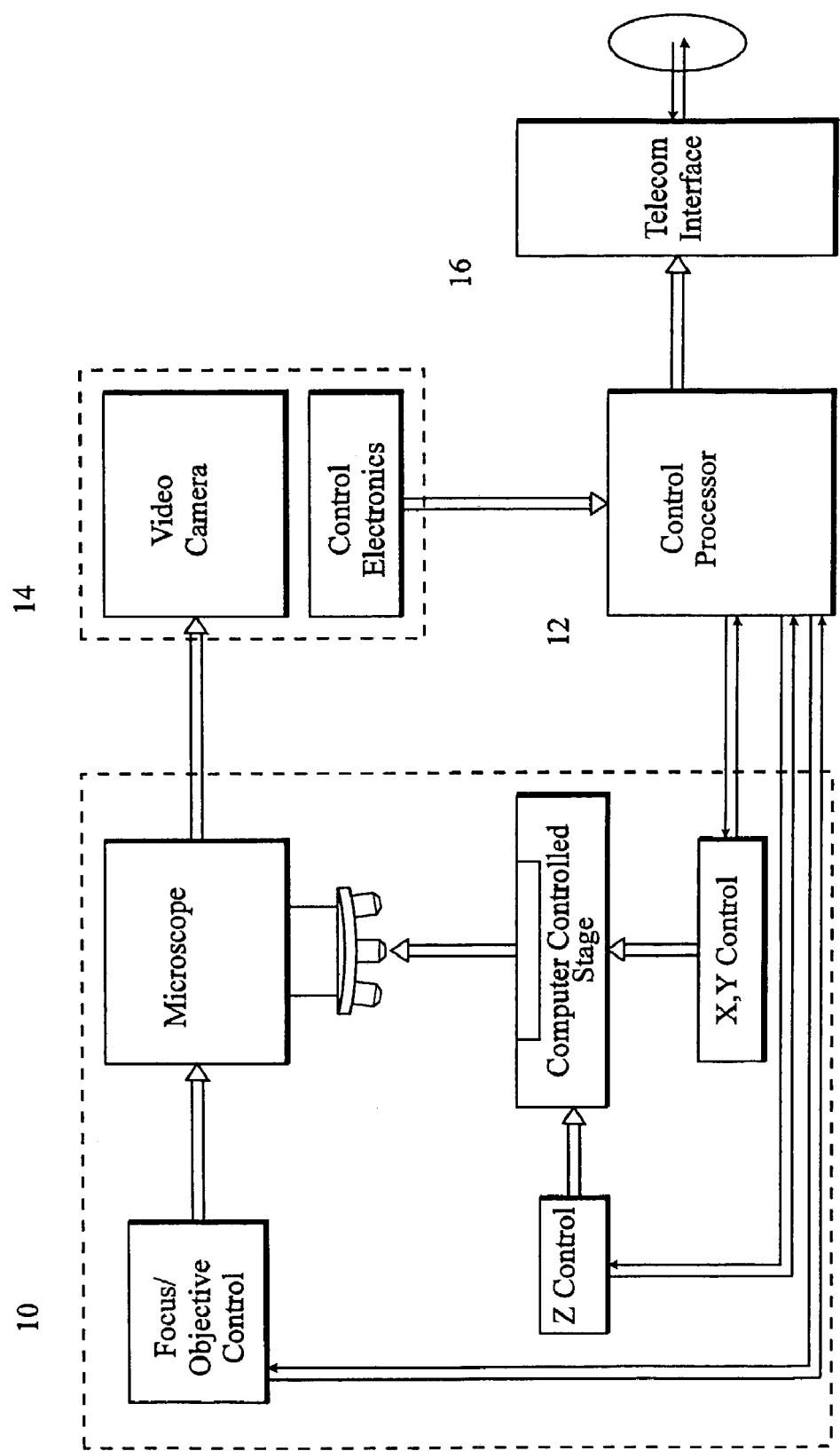
FIG. 1 is a semi-schematic block level diagram of a host network server platform, including a telemicroscopy system in accordance with practice of principles of the present invention.

In order to gain a complete understanding of the compression packaged image transmission system and method of the present invention, it will be useful to examine how the system might function in the context of a typical telepathology procedure. During the course of a surgical intervention, as a surgeon is preparing to perform an invasive procedure, the surgeon will typically remove a sample of tissue from a patient and forward the tissue sample to the hospital's diagnostic laboratory for immediate evaluation. The tissue sample is prepared in conventional fashion and loaded onto the sample stage of an examining microscope, comprising the laboratory's telemicroscopy system, where an image of the tissue sample is captured by a video camera and electronically communicated to a pathologist at a remote site for evaluation. During the initial, or preliminary, evaluation, a pathologist is able to view the tissue sample in macro and is further able to give directions to laboratory personnel as to location and direction of sectioning to be performed in order to further any subsequent diagnosis. Frozen sections are prepared according to the guidelines of the pathologist, the sections are mounted on glass slides, appropriately stained, and subsequently loaded onto a robotically controlled microscope stage of the telemicroscopy system. Control of the telemicroscopy system is then given to the remote-site pathologist.

The remote site pathologist is able to manipulate all of the microscope's features and view images appearing under the microscope objective as though the pathologist were present at the laboratory site and directly manipulating the microscope. Motion control of the microscope stage in X-Y directions, as well as focus control of the stage in the Z direction, is performed by issuing the appropriate control commands to a remote site small platform computer system which, in turn, transmits motion control commands to the telemicroscopy system in the hospital laboratory. Following each X and/or Y translational movement of the microscope stage, the resulting tissue sample image is transmitted to the pathologist's remote site, where it is displayed on a high resolution monitor. The pathologist is, thus, able to manipulate and view a tissue sample as if the microscope containing the specimen were directly in front of him.

Following the pathologist's investigation, the pathologist can prepare a report which provides the surgeon with his diagnostic opinion in the case, either over the same bi-directional communication medium used to examine the specimen, or by any one of a number of various other electronic communication forms available to the pathologist. In particular, the pathologist may transmit a written protocol to the surgeon by facsimile, e-mail, and the like, or make a direct oral report to the surgeon and follow-up with written documentation communicated electronically. After making a diagnosis, the pathologist releases the telemicroscopy connection and is then available for a next consultation with some other surgery team which might be preparing to perform a different surgical procedure in a totally different location. In the meantime, the original consulting surgeon is able to continue the intervention procedure according to the outcome of the diagnosis made by the pathologist. As a check, the original consulting surgeon may decide to forward the original tissue specimen to a local pathology laboratory for a final diagnosis, in accordance with conventional accepted procedure. This manner of "Gold Standard" cross-checking, is particularly useful as a means of acquiring data on the accuracy of results obtained by formulating diagnostic opinions on the basis of televised images which have been compressed, transmitted over long distances over relatively "noisy" communication connections, decompressed and viewed on a high resolution video monitor screen.

In this regard, it bears mentioning that if visual image data can be transmitted to a remote site pathologist for the purpose of obtaining a diagnostic opinion, the same visual image data can be transmitted to a consulting pathologist, by either the primary diagnostician, or the hospital. A primary and a consulting pathologist, or more than one consulting pathologist, are able to confer with respect to the same visual image data representing the tissue sample. The ability to obtain on-line consultations is extremely advantageous, particularly where the proposed intervention implies a tissue morphology requiring the services of a pathologist or pathologists having a highly developed and correspondingly rare sub-specialty Turning now to FIG. 1, there is depicted a simplified semi-schematic block diagram of an exemplary host or server telemicroscopy system useful in the practice of the present invention. FIG. 1 illustrates the primary components of a remote, or robotically, controllable telemicroscope, operable under software program control which would be hosted on a control processor such a small platform personal computer system. In accordance with the invention, telemicroscopy equipment connected to a telecommunication net in accord with a bi-directional communication protocol, forms a key enabling tool for establishing effective telemedicine services. This allows the system to combine the high-resolution and color saturation integrity of digital, still video images with the ability to establish bi-directional communication between the "server" and a "client" system to enable remote, client control of the microscope in real time. Acquisition and transmission of high-resolution video images of desired portions of a specimen can be performed in a time period consistent with hands-on, real-time optical practice.

The telemicroscope portion, indicated generally at 10 suitably comprises a remotely controllable microscope 12 configured with an illuminated, robotically controllable microscope stage 14. The microscope stage is movable in X and Y directions and is controllable from a remote source by mechanically coupling X and Y translation motors to the stage platform through control circuitry 16. A suitable illumination source is disposed beneath the stage and is also translationally movable beneath the stage in order to shift the apparent illumination source with respect to a specimen on the microscope stage. Both the translational motion and intensity of the illumination source are remotely controllable under software program control operating as an application on the control processor.

A plurality of objective lenses 18 are connected to a rotatable objective frame such that a specimen may be viewed at various magnifications. The rotatable frame may also be robotically controlled such that the various objective lenses can be moved into the microscope optical path and a specimen be viewed under any one of a number of magnifications at the desire of the operator. Examples of robotically controlled microscopy systems suitable for use in connection with the present invention include the Olympus Vanox microscope system equipped with a Prior H100 remotely controllable stage, or other similar computerized stages such as those manufactured and sold by Opelco.

A control processor, indicated at 20, implemented as a small platform computer system such as an IBM-type x86 personal computer system, provides the data processing and platform capabilities for hosting an application software program suitable for developing the necessary command and control signals for operating the microscope system. The control processor 20 is able to receive and interpret commands issued by a system user on a conventional input device, such as a mouse or a keyboard, and convert user defined commands into signals appropriate for manipulating the various components of the microscope system. The control processor 20 is typically coupled to the microscope system through an interface, such as an SCSI interface, a proprietary interface or any one of a number of alternative coupling interfaces, which, in turn, defines a system bus to which the various control electronics operating the microscope system are connected.

A magnification control system suitably comprises a robotically controllable motor and motor driver combination which is coupled to the objective frame and is configured to rotate the frame to bring various desired objective lenses into the optical path. Upon receipt of an appropriate movement command signal, the magnification control system directs the motor to rotate the rotatable frame, thus moving a different objective lens into the optical path of the microscope system. Stage movement is likewise robotically controlled by a stage movement control system 16 which also comprises motors for moving the sample stage 14 in the X, Y (16) and Z (17) directions along with appropriate motor driver circuitry for actuating the motors. The mechanical apparatus and electronic control circuitry for effecting stage movement is preferably implemented to include some form of open or closed-loop motor positioning servoing such that the sample stage can be either positioned with great precision, or its translational movement can be determined very accurately in the X, Y and Z directions. For reasons that will be described further below, it is important that the microscope stage respond precisely to movement commands and that stage movement can be very precisely determined and carefully controlled.

When the stage control system is configured to operate closed-loop, position feedback information can be recovered from the motor itself, or from optical position encoders or laser interferometer position encoders, if enhanced precision is desired. Closed-loop servo control of stage motion allows the stage position to be determined with great accuracy and insures that translation commands are responded to with great precision. Thus, a command to translate the stage 50 microns in the positive X direction will result in the stage moving precisely 50 microns in +X, at least to the mechanical resolution limits of the motor system.

If the system is configured to operate semi-closed-loop, or open-loop, stage control is not dependent on feedback per se, but it is at least necessary to precisely define where the motors controlling the stage were told to go. For reasons detailed further below, the transmitted video image is compression packaged in a manner that takes stage motion (both relative degree and absolute magnitude) into account when defining the compression packaging technique used under various circumstances.

Focusing is performed by causing small excursions of the stage in the Z direction under control of corresponding focus control circuitry 17. Because the amount of relative motion during focusing is significantly smaller than the amount of relative motion during gross Z translational movements, the focus circuitry may well comprise a microstepping motor controlled by appropriate motor driver circuitry and operating in parallel with the Z axis stage translation motor. The z axis translation motor could, thus, be provided with a more gross response characteristic so that it would be able to accommodate vertical optical sectioning of a specimen, i.e., viewing a specimen on various horizontal planes vertically disposed therethrough, while the focusing motor would accommodate the micromotions required to adequately focus each image plane. Illumination circuitry controls the intensity of the illumination light source in conventional fashion.

A video camera 22 is optically coupled to the microscope to capture diagnostic-quality images of microscopic tissue samples disposed on the sample stage. The video camera 22 is preferably a high resolution, color, digital video camera operating at an image resolution in accordance with, at least, the NTSE standardized composite color video image specification. Examples of video cameras suitable for use in connection with the present invention include the Sony DKC-5000 series of video cameras, the Ikegami 370-M video camera, and other makes and models of composite, color video cameras of comparable quality and resolution. Images captured by the video camera 22 are directed through video image processors 24 whereby they are able to be displayed on a high resolution digital display screen coupled to the telemicroscope control processor 20.

In addition, and in accordance with the present invention, high-resolution video images captured by the camera are compression packaged by the control processor 20 for transmission over a telecommunications interface 26, coupled, in turn, to a wide-area-network 28 such as the Internet.

The images developed by the video camera should have at least the resolution available under the NTSC standard. In North America and Japan, the NTSC color video image comprises approximately 480 pels per image scan line in the red, green and blue (RGB) color components. Approximately 480 scan lines comprise an image frame, and image frames are generated at a rate of approximately 30 frames per second. If each color component is coded as an 8-bit value (24 bits/pel, i.e., "true color") representing some form of luminance plus color difference encoding, for example, the representing continuous composite video is produced at a bit rate of about 168 Megabits per second (Mbps). For truly high resolution image production suitable for telepathology applications, the video camera should be able to generate still images with resolutions preferably in the range of from 800×600 (pels×lines) to about 1024×1024 (pels×lines). These images are transmitted at frame rates of 30 fps and, at 24 bits per pel, this results in an image bit rate in excess 750 Mbps.

Clearly, the effective bandwidth of the electronic telecommunications network connection which interconnects the host server system with a pathologist's remote viewing and diagnostic facility (termed herein a client system), determines the amount of time, or intrinsic delay, required to remotely display transmitted high resolution images on a high resolution monitor in a form and of a quality suitable for telepathology applications. Ideally, the system and method of the present invention are implemented as an application software program, hosted on both a hospital's host server and a pathologist's client system. The application program should be independent of the communication links interconnecting various sites, and should be capable of operation over a wide variety of conventional local and wide area network (LAN and WAN) architectures. Preferably, the system is configured for optimum performance as a Windows-based TCP/IP implementation, compliant with the WinSock 1.1 specification, and is thus compatible with LAN-over-broadband telecommunications architectures such as an Asynchronous Transfer Mode (ATM) based optical fiber connection.

Basic rate ISDN, bundled ISDN, Asymmetric Digital Subscriber Loop (ADSL) and various Frame Relay telecommunications links are also contemplated as electronic communications interconnections suitable for use in connection with the system present invention. Although ATM-based communication protocols in conjunction with an Internet-based interconnect architecture is preferred, all that is really required is a communication architecture (connect hardware and data transmission methodology) able to bi-directionally communicate digital data at bitrate appropriate to the invention. The actual communication bandwidth required will, of course, depend on the kind and amount of compression applied to the raw video data stream. As will be developed in greater detail, below, compression packaging the video data stream in accordance with the invention results in effective bit rates sufficiently low enough to make effective use of many LAN/WAN architectures.

Figure 2:
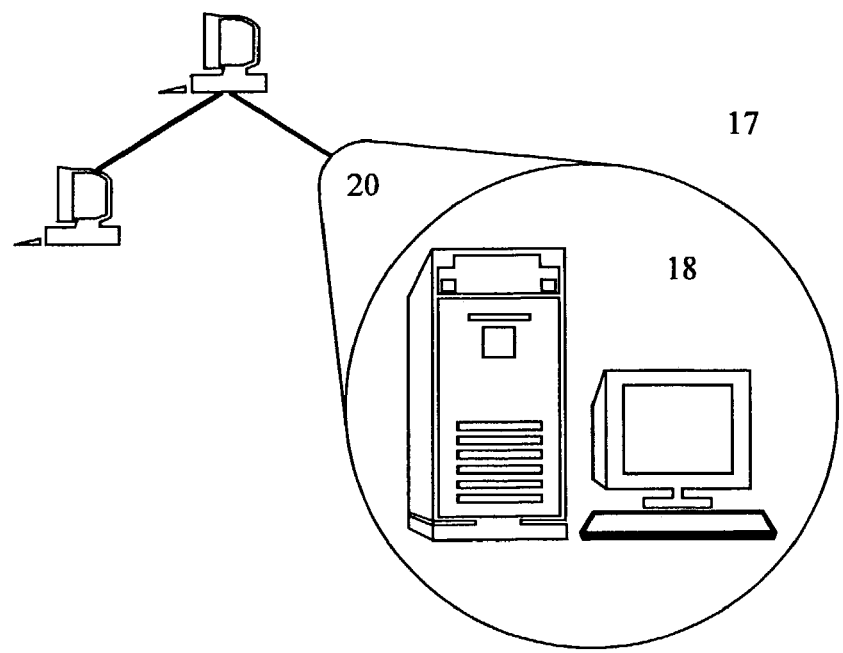
FIG. 2 is a semi-schematic block level diagram of a network client system useful for hosting a remote site telepathology application in accordance with practice of principles of the present invention.

FIG. 2 depicts, in semi-schematic block diagram form, an exemplary client system which would typically be employed in the clinical practice facility of a pathologist. The client system simply comprises a typical personal computer system 30 equipped with a large, preferably 17 inch or larger, high-resolution monitor system, 32, operatively controlled by a high-resolution, high-quality video graphics display subsystem hosted by the system's electronics housing 34. A suitable implementation of the client PC system would include a high speed processor, such as the Intel x86 series processor, sufficient random access memory to host the necessary application software, a mass storage device such as a hard disk drive, and communications interface circuitry for effecting direct electronic communication with the server application of FIG. 1. Optionally, the client system might be provided with a video conferencing suite including a video conferencing camera, a microphone, speakers and electronic interface circuitry, such that the client user is able to effect bi-directional audio/visual communication with the server site in parallel with the sample video transmission.

Ideally, the pathologist's client system would operate within a Windows® or Windows-like graphical user interface (GUI) based environment in order to best take advantage of the preferred Internet-based bi-directional communication system in accordance with the invention. Operating within the familiar graphical Windows-based environment, the pathologist is able to control the remote telemicroscopy system by merely "clicking" on various commands available through menus, or submenus, presented by the application software in a manner which mimics conventional Web-browser application software. Alternatively, the GUI environment would allow image tracking and movement commands to be generated by "clicking" directly on the screen image. All of the telemicroscope controls are available to the pathologist by using simple mouse commands, or alternatively, by issuing simple step commands over a keyboard. Multimedia functionality allows for bi-directional audio communication between the pathologist at the remote site and clinical personnel at the telemicroscopy server, so that the pathologist is able to converse with laboratory technicians, issue directions, make suggestions and the like, all in parallel with the video feed. The Windows® or Windows-like interface for microscope control and image display remains active throughout the entire session, for continuous ease of use.

The methodology of the present invention is preferably implemented as an application software program running on both the telepathology network server and a pathologist's client system and is adapted to both control a telemicroscopy system and receive information from a video camera connected thereto. A microscope slide containing an investigation section is placed on the robotically controlled sample stage of the server system's telemicroscope. In one particular embodiment of the invention, the server system might initially create a "mosaic" of smaller images which are arranged in a grid, or tiled, to define a complete low power image of the entire tissue specimen to be examined. As a pathologist initiates an electronic communication with the server system, the mosaic image of the sample becomes available and is stored on a mass storage media device such as a hard disk drive on both systems for future reference. The pathologist may use the mosaic image as a reference image or "roadmap" for further evaluation of the sample and is able to select any area of the mosaic for viewing at higher optical magnification. As will be described in greater detail below, the mosaic is initially transmitted with a particular level of detail, i.e., magnification resolutions of from 1× to about 10× are immediately available for viewing. As additional resolution is desired, resolutions greater than 10×, for example, only the additional resolution detail required for examination of that particular mosaic "tile" is transmitted, representing a significant bandwidth savings.

As the pathologist determines which portion of the mosaic to investigate, higher optical magnification is obtained by issuing the appropriate commands over the client system, which are transmitted to the server system through the network's communication connection. Additional portions of the mosaic are captured for viewing by issuing the appropriate commands to move the remote sample stage of the telemicroscope to appropriate X-Y positions which correspond to a selected location on the low power mosaic image. Selection of particular locations for further viewing might be accommodated by "clicking" on the selected location using a mouse and further "clicking" on a desired magnification factor provided on a menu. All images transferred to the client system remain on the display until no longer required. All images may further be archived in a database along with their X-Y coordinates with respect to the mosaic image, a time stamp, illumination data, and any such other information required to reconstruct the pathologist's diagnostic "trajectory" through the specimen. These archived images are particular useful in developing a database for clinical education purposes.

Once the pathologist has determined where to begin examination of the specimen, sample magnification is increased to an amount appropriate for examination of detail and transmission of detailed video data is initiated in accord with the invention. Video data is transmitted to the client system according to an adaptive, multi-tiered compression methodology which dynamically adapts the form, content and detail of transmitted images to the visual perception abilities of a typical system user. To summarize, if a user is unable to perceive image detail because, for example, the image is moving due to sample stage translation, the image is adaptively transmitted at a significantly lower resolution, i.e., using significantly lower bandwidth. As the image stabilizes, and higher resolution is perceptible, the system adaptively increases transmitted detail. Thus, the system inherently delivers detail proportional to a user's ability to perceive that level of detail.

The system is termed multi-tiered, in that various forms of compression, both cognitive and operative, are used to define the transmitted image data. For purposes of illustration only, an exemplary embodiment of the invention will be described in terms of a three-tiered compression system in which the tiers comprise; first, necessary image transmission; second, progressive image encoding, and; third, bitwise image compression, exemplified by the JPEG still image compression standard.

In operation, when a pathologist selects a particular sample portion for detailed viewing and requests the sample stage to move in the X or Y direction, the server system controls stage movement according to appropriate commands received from the client via a special-purpose TCP/IP network protocol. It should be noted, here, that this network protocol is merely an extension of HTTP and is configured to support application-specific protocols relating to session management, hierarchical image decomposition, image compression, data transmission and telemicroscopy control commands. These commands include translating the sample stage in the X or Y direction in order to alter the relative X-Y position of the camera with respect to the stage and, thus, the specimen or frozen section. When the pathologist requests stage movement in the X or Y direction, the client system issues this request to the telemicroscope through the server, the telemicroscope system moves the stage and a new portion of the section is brought into view. It is important to realize that when the sample stage is moved, the prior image is effectively translated in the X and/or Y directions by a specific amount, defined by the pathologist working at the client system.

Figure 3:
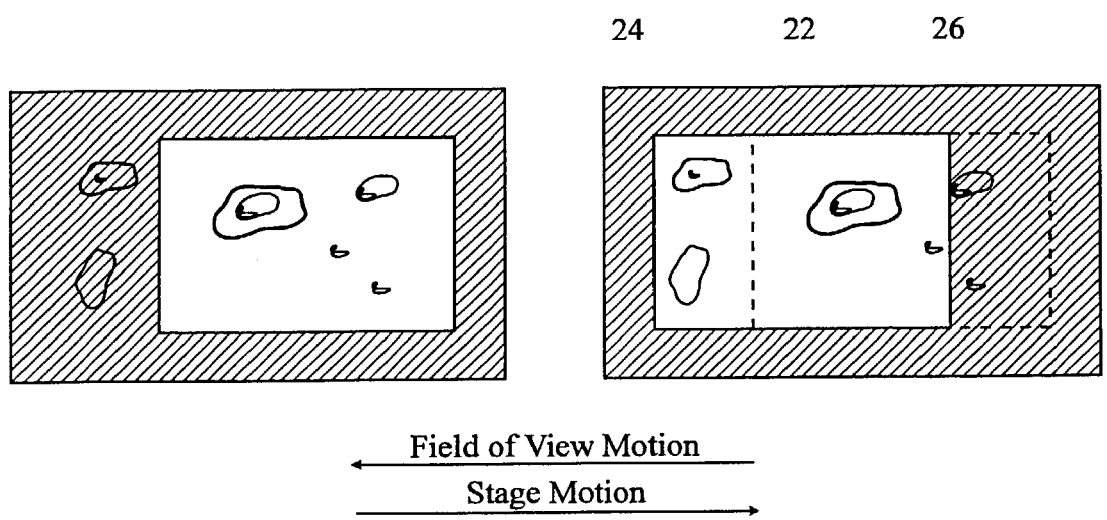
FIG. 3 is an exemplary illustration of microscope sample stage translational motion defining previously transmitted and new portions of a telemicroscope field of view.

As illustrated in FIG. 3, as an image is translated, the resulting new image may be decomposed or defined in terms of two image portions; a first portion 36 comprises those parts of the prior image which remain in the field of view but have been translated by an amount determined by the X and Y stage motion commands (termed herein previously transmitted portions) and those portions of the image 38 which have been translated into the field of view and which constitute previously unseen and, thus, untransmitted information (termed herein new portions). In accordance with the present invention, the client system is able to calculate to what degree the previously transmitted image portions must be displaced in the X or Y direction in order to reflect the translational movement commands directed to the sample stage. Those previously transmitted portions are merely displaced in the display system with those sections which presently fall outside the field of view being "dropped-off" the edges in the direction of translational movement, as indicated in FIG. 3 at 40.

It will be understood by those having skill in the art that those previously transmitted image portions 36 which remain in the present field of view need not be retransmitted by the server system, but need only be analyzed and displaced by the client. Those portions of the new image which were not previously transmitted, i.e., the new portions 38, are the only image portions which require transmission. This necessary image transmission procedure results in a significant bandwidth savings when translational motions in both the X and Y direction are relatively small, requiring a significantly reduced amount of image information transmission in order to define the new field of view. Once the new image portions have been determined, those image portions are designated for transmission and may be either directly transmitted in a PKZIP-type bitwise compression format, for example, or alternatively, compression packaged in accordance with the system and method of present invention and subsequently transmitted as a compressed bitstream.

The progressive encoding tier of the multi-tiered compression scheme is typically invoked when sample stage translational movement is fast enough that entire frames, or substantial portions of frames are "dropped off" such that the majority of the image comprises a "new" image portion. In this case, the image is subject to a progressive encoding scheme based on differential subsampling. In accordance with the invention, image sampling would only be performed with respect to every other pel, for example, in both X and Y. Taking only half the pels in both the X and Y dimensions, typically results in a reduction in the image size by about 75%. However, overall image size can be maintained by merely replicating each pel in software, at the receiving (client) site, resulting in a full-size image having one-fourth the original resolution density. In a 1024×1024 system, this factor-two progressive encoding scheme would result in an image having the effective resolution of a 512×512 original. This resolution level is certainly acceptable for fast panning and is also marginally acceptable for "quick-stop" fast impressions.

Once panning is concluded (i.e., when the system no longer "sees" X and/or Y translation commands being issued to the server), the unsent portions of the video signal are transmitted in background, and are used to fill-in the image in place of the replicated pels, until the ideal 1024×1024 resolution is reached. Needless to say, the subsampling index can be selected by the user through a settable system parameter. The progressive encoding tier is able to be programmed to sample every other pel, every third, every fourth, etc. according to the perceptual desires of the user. Lower value indices, while increasing resolution during fast panning, do so at the cost of bandwidth and should be invoked only after careful consideration.

Figure 4:
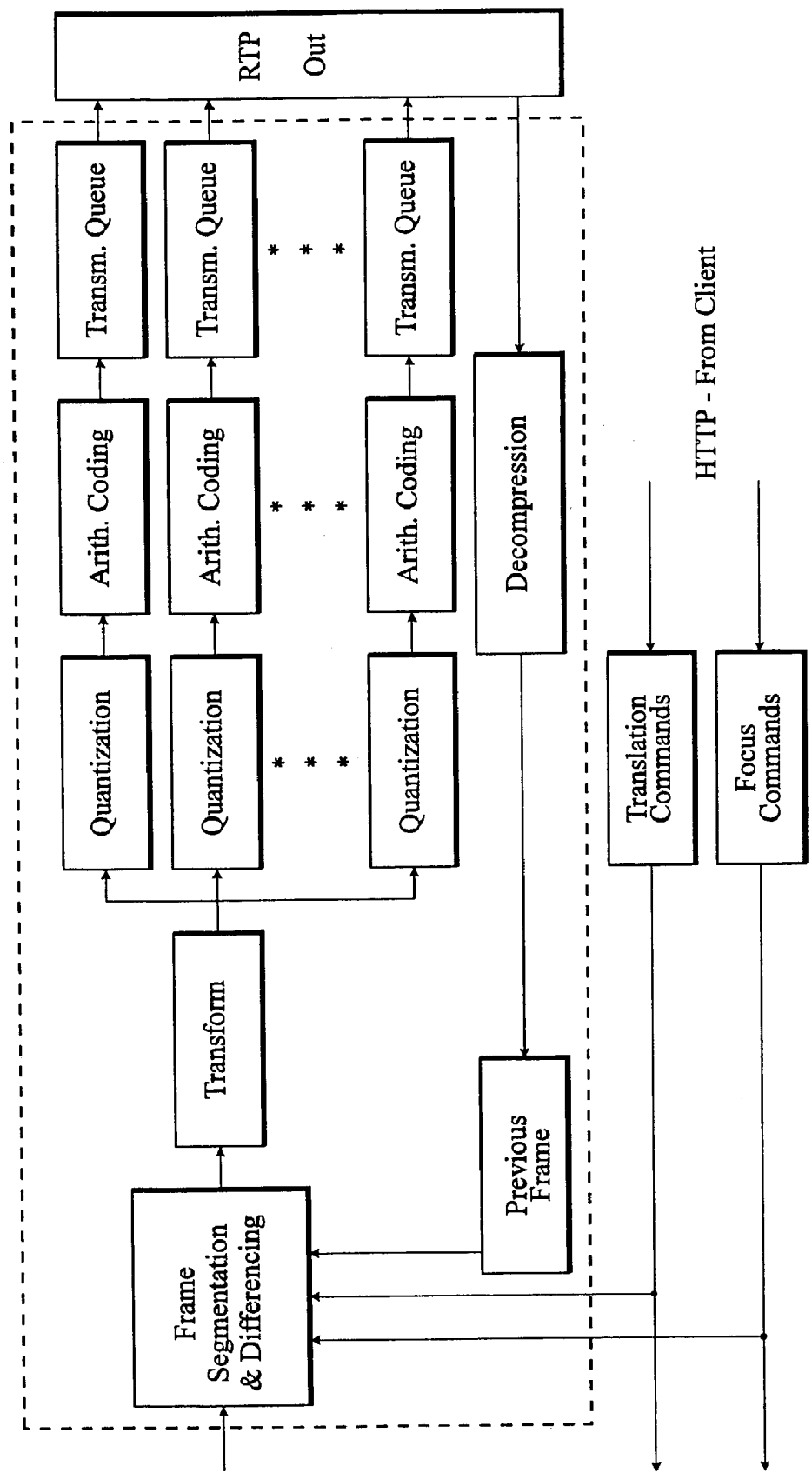
FIG. 4 is a semi-schematic simplified block diagram of one embodiment of a video image transmission system including multi-tiered compression according to the present invention.

Turning now to FIG. 4, which is a semi-schematic block diagram representation of a bitwise compression encoding and packaging engine in accordance with the practice of principles of the present invention, video data representing a frame of video information is captured by a video camera and initially provided to a frame segmentation and differencing engine 42. Briefly, the frame segmentation and differencing engine 42 is responsible for the first compression step, i.e., identification of those portions of the video frame which are "new" and, thus, necessary for transmission. Frame segmentation and differencing can be best understood as the process of comparing a present video frame with an immediately previous video frame, represented at 44, and determining which portions of the previous frame are to be retained, which portions of the previous frame are to be discarded for transmission purposes and which portions of the present frame represent new image data requiring transmission. With regard to identifying those portions of the previous frame which are to be retained, the frame segmentation and differencing engine 42 is further able to define the displacement vector difference between the present and previous frames by analyzing position and focus change commands directed to the telemicroscope system.

In accordance with the invention, the previous frame video data 44 is provided to the frame segmentation and differencing engine by retrieving the previous frame data from server system memory and decompressing the data using a decompression engine 46 to, thereby, redefine the raw video information defined in the previous frame. Previous frame data is "overlaid" to the present frame data in software to define those "new" portions which require transmission.

Following frame segmentation and differencing, the "new" portions of the present video frame data is compressed, in a transform block 48, in accordance with any one of a number of lossy compression techniques, such as the Discrete Cosine Transform (DCT), as implemented in the JPEG compression standard, wavelet transform coding, and the like. Whether lossy compression is performed using Discrete Cosine Transforms or wavelet transform coding, the techniques result in the video image being represented as a set of coefficients representing the contributions of various frequency components of the signal. Once decomposed into their various frequency components, frequency component coefficients are "packetized" and inserted into a number of transmission queues 50 which, in a manner to be described in greater detail, are assigned to transmission priority levels based on the level of detail which each packet additively contributes to the resultant composite image. In the case of the Discrete Cosine Transform or a wavelet transform, the lower frequency components represent the least amount of image detail and packets which define lower frequency component coefficients are, accordingly, assigned the highest transmission priority. As detail, and thus, frequency, increases, packets containing higher frequency component coefficients are assigned correspondingly lower transmission priorities until, in the limit, the highest levels of detail (the highest frequency components) are assigned the lowest transmission priority.

Packetization and prioritization of transform encoded frequency data is an important aspect of the present invention, since it allows transmission bandwidth to be adaptively varied in order to accommodate the subjective, perceptual aspects of a moving image system. For example, when sample stage motion is being executed quickly, i.e., relatively large amounts of X and/or Y translational movements, only those coefficient packets representing the lowest frequency components of the image, are transmitted to the client system for display. It will be understood that if stage movement is rapid, a viewer is unable to perceive fine detail making it unnecessary to burn bandwidth or channel capacity attempting to transmit volume data relating to imperceptible detail. It is understandably more important to service the client system with faster overall frame updates which might be detail deficient than it is to service the client with specimen detail at considerably slower intervals.

As stage movement is slowed down, i.e., as X and/or Y translational movements become less, additional transmission queues are flagged for transmission and bandwidth that is not being used to send new fields of view is available for transmission of additional packets comprising higher frequency component coefficients for the current view. Adding the information from additional transmission queues necessarily enhances the detail of the current image being displayed by the client system. Necessarily, as translational movement of the sample stage ceases, all that remains is for the final transmission queues, comprising the highest detail level component coefficients, to be flagged for transmission to the client system.

The information contained in these final transmission queues may make use of all of the available transmission bandwidth since lower frequency information (higher priority packets) have been previously transmitted. It will be understood by those having skill in the art that image detail is accordingly inversely proportional to stage translational movement speed, with higher speed movement resulting in lower image resolution. Thus, the compression encoding procedure in accordance with the invention is able to inherently deliver image resolution or detail in proportion to the resolution level that is able to be perceived by a viewer., Compression encoding and adaptive prioritization of image resolution packets defines an image system that is able to efficiently build upon previously transmitted data in order to minimize transmission time (maximize bandwidth) for a full resolution image.

Returning now to FIG. 4, transmission queues 50 containing prioritized frequency component packets, are optionally preceded by components that are configured to provide an additional degree of either lossy, or lossless compression encoding to each of the respective component coefficient packets defined by the transform engine. These optional components might suitably comprise quantization engines 52 followed by arithmetic coding or entropy coding engines 54. Both quantization and arithmetic or entropy coding are options available in the JPEG standard and need not be described in detail herein. Specifically, baseline JPEG uses Discrete Cosign Transform compression of 8×8 blocks of pels, followed by scalar or vector quantization of the DCT coefficients and entropy encoding of the result. JPEG specifies two possible entropy encoders, one of which is based on the well understood Huffman coding algorithm and which is required for the baseline JPEG system. Extensions to the JPEG standard and JPEG lossless compression modes also permit the use of arithmetic coding, exemplified by the IBM Q-Coder, as an alternative.

Compressed video image data is then moved through the server system whence it is transmitted to the client application over a broad band telecommunications architecture via an ATM-based communication channel 56 using, for example, IP-over ATM LAN emulation. While transmission queues are forwarding various components of the video image data to the client system, the server application is able to receive telemicroscope stage translational motion commands and/or focus commands from a pathologist at the client, through translation command circuitry 58 and focus command circuitry 60. If a particular stage translational movement is requested that moves a portion of the current image out of the field of view, coefficient packets that correspond to those blocks comprising that portion of the image are flagged with an identification tag which indicates that these packets are no longer in the field of view and, accordingly, need not be transmitted.

It will be understood, of course, that in the case of Discrete Cosine Transform compression, block sizes will be in the familiar 8×8 form. In the case of wavelet transform compression, wavelet blocks are variably sized, and typically larger than the 8×8 DCT standard. It will be understood by those knowledgeable in the art, that common practice would normally be to apply the wavelet across the entire new image portion strip, thereby defining the block size as the new image portion. While this practice maximizes compression efficiency, it does so at the expense of packetization and prioritization efficiency. It should be further understood that the new image portion can be subdivided into subimages with each of the subimages wavelet transformed in order to improve efficiency of the flagging process (packetization and prioritization). Necessarily, this will be at the expense of some compression efficiency. Ideally, wavelet blocks are sized variably in accordance with a design choice that achieves a desired balance between out-of-view flagging and wavelet transform performance efficiency.

In the case of changes to specimen focus, i.e., stage motion in the Z direction, large portions of the currently displayed image undergo substantial modification. The new image, resulting from a focus change or a change illumination intensity, is subtracted from the previously transmitted image represented by the previous frame data in the frame segmentation and differencing engine, resulting in an image comprised of the difference between the previous frame and present frame as seen by the video camera. The difference image is then transform coded by the transform engine and the resulting lossy compression packaged data is then optionally quantized and/or entropy or arithmetically coded for transmission.

Figure 5:
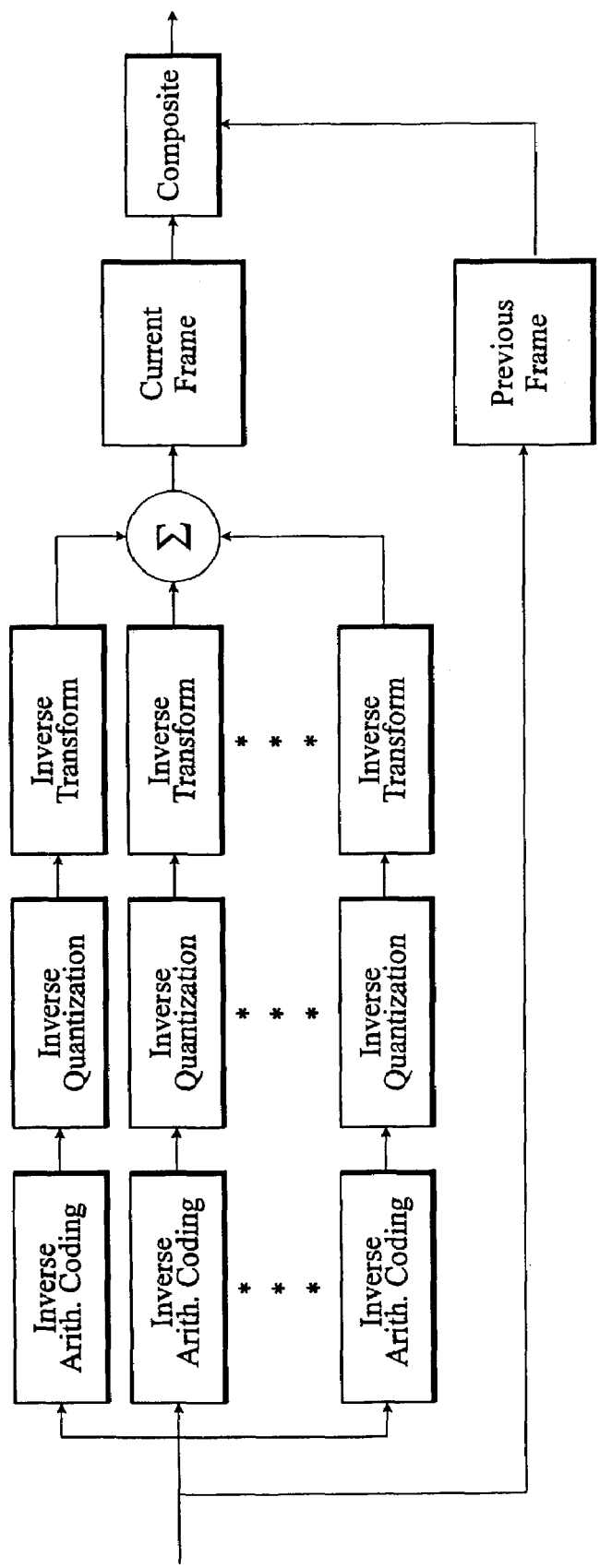
FIG. 5 is a semi-schematic simplified block diagram of a decompression system adapted to receive compression packaged video image transmissions in accordance with the invention.

As is shown in the semi-schematic block diagram of FIG. 5, transmitted video data is decompressed in accordance with an inverse sequence of processes and the resultant inverse transform data is summed to define the current video frame. In a manner similar to frame segmentation and differencing, a composite picture 66 is built up by adding current frame data 62 to retained portions of the previous frame data 64 which have been displaced, in software, in accordance with any translational motion or focus vector changes. The resulting composite frame 66 is then sent to the videographics client for rendering on the display screen. Received compressed video information is decoded in respective inverse arithmetic coding engines, from whence the data is directed to inverse quantization engines 70. Each packet is then reconstructed in accordance with an inverse transform, in respective inverse transform engines 72, and summed, in a summing circuit 74, to become the current frame representation 62 of the image.

It has been determined that the multi-tiered compression packaged image transmission system in accordance with the invention is able to deliver video image data at an effective compression rate of approximately 1:400. Given a raw video input signal comprising a 1024×1024 pel×frame produced at a frame rate of approximately 30 frames per second, with each pel represented by a 24 bit (true color) digital value, the raw data stream would be operative at approximately 755 Mbps. Assuming a ⅔ screen width pan taking place in 0.25 seconds, the multi-tiered compression system according to the invention would be providing video data to the client system at an effective rate of about 1.65 Mbps when all of its component portions are considered.

The necessary image transmission portion of the novel compression system accounts for at least an order of magnitude reduction in the effective bit rate; 755 Mbps reduced to 66 Mbps. Transform coding and prioritization queuing of the resultant output stream results a further 40 to 1 reduction in the effective bit rate; from 66 Mbps to about 1.65 Mbps, with progressive encoding accounting for a 4:1 reduction in the bitstream (from 66 Mbps to about 16.5 Mbps). It should be noted that this last value represents a two-fold improvement over the generally accepted standard JPEG capabilities. Without being bound by theory, it is thought that the major portion of the improvement results from the ability of the novel system to adaptively deliver image detail in inverse proportionality to sample stage movement speed and in direct proportionality to the degree of detail that can be perceived, while at the same time, building detail upon previously transmitted data for transmission bandwidth utilization efficiency.

The necessary image transmission portion of the novel compression system accounts for at least an order of magnitude reduction in the effective bit rate; 755 Mbps reduced to 66 Mbps. Transform coding and prioritization queuing of the resultant output stream results a further 40 to 1 reduction in the effective bit rate; from 66 Mbps to about 1.65 Mbps, with progressive encoding accounting for a 4:1 reduction in the bitstream (from 66 Mbps to about 16.5 Mbps). It should be noted that this last value represents a two-fold improvement over the generally accepted standard JPEG capabilities. Without being bound by theory, it is thought that the major portion of the improvement results from the ability of the novel system to adaptively deliver image detail in inverse proportionality to sample stage movement speed and in direct proportionality to the degree of detail that can be perceived, while at the same time, building detail upon previously transmitted data for transmission bandwidth utilization efficiency.

While the foregoing has included a description of the present invention in connection with an exemplary telemicroscopy application, it should be understood that principles of the invention are equally applicable to image transmission methodologies that encompass various combinations of lossy and lossless image compression, particularly when adapted for image transmission and archiving purposes. Taking the principles of the invention into account, i.e., image transmission and display is predicated upon the ability of a viewer to perceive the degree of detail present in a particular image, image compression is subdivided into lossy and lossless image compression stages, with image portions being transmitted from various queues in accordance with viewer perceptualability. In the present context, lossless image compression is commonly understood to refer to compression techniques that allow a particular image, when decompressed, to be replicated precisely, at a bit-by-bit comparison level, in the same form as the original image. Particular types of lossless image compression algorithms might include run length encoding (RLE), Huffman coding, dynamic Huffman coding, Lempell-Ziv-Welch encoding, and the like. While many lossless compression techniques do afford some degree of compression, i.e., some degree of bandwidth recovery, lossless compression techniques do not typically afford sufficient bandwidth recovery for rapid image transmission over commonly implemented transmission channels. Thus, lossless image compression, while accurate, is slow.

Lossy compression techniques result in a recovered image that is not precisely the same, at a bit-by-bit comparison level, as the original image. Lossy compression techniques result in a significantly higher degree of bandwidth recovery than lossless techniques, but the amount of precision detail available in the resultant image is often insufficient for high magnification applications such as telemicroscopy, and the like.

With the advent of Internet-type wide area networking, many applications that were previously limited to local use, i.e., direct high-speed access to a local memory storage area such as a local hard drive, are now being implemented by systems separated by great distances geographically. Many of these applications, such as fluorescent imaging, CAT imaging, and the like, involve quantitative analysis of the image. Accordingly, it is necessary that the final image remain "lossless" upon compression without unduly interfering with bandwidth constraints of remote viewing and data archiving.

Figure 6:
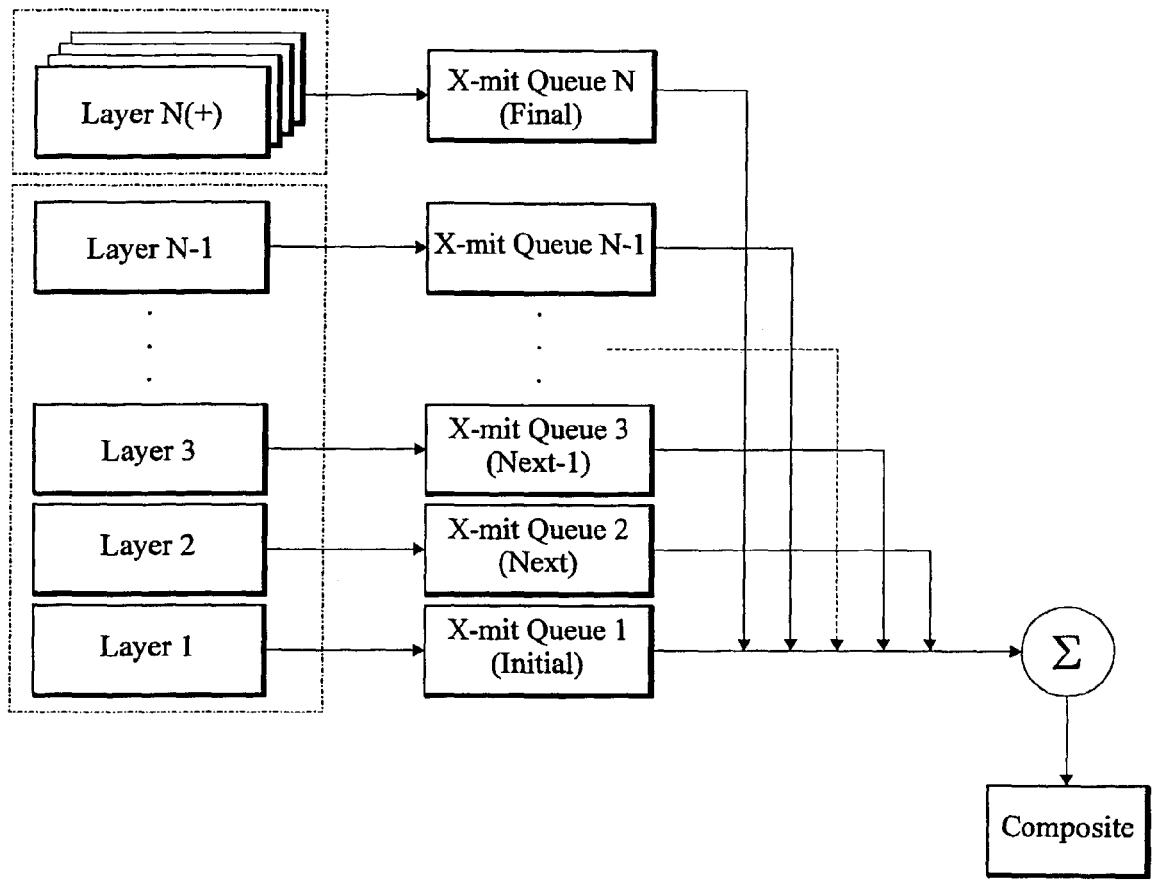
FIG. 6 is a semi-schematic simplified block diagram of an additional embodiment of a layered decompression system in accordance with the invention.

Turning now to FIG. 6, a particular advantage of the principles of the present invention is that lossless compression of images for both archiving and transmission purposes may be achieved without sacrificing transmission speed when images are accessed by a remote location. As can be seen from the exemplary embodiment of FIG. 6, lossy and lossless compression techniques are layered, with the various layers representing increasing amounts of detailed structure available for a particular image. In FIG. 6, the coding layers are divided into a lossy layer portion 100 and a lossless layer portion 102. The lossy layer portion 100 is further subdivided into a plurality of layers, represented by ordinal identifiers ranging from 1 to N−1, as indicated in FIG. 6. According to the invention, lower ordinal layers 1 to N−1 are adapted to contain data obtained from a lossy compression methodology such as a direct cosine transform (DCT), a wavelet transform, fractal compression, and the like, as was described above. Coefficients arising from such transforms are quantized and prioritized into the various lower ordinal lossy layers 100, as was described previously in connection with the embodiment of FIG. 4. Prioritization, necessarily, is expected to vary from application to application, with coefficients being typically classified in accordance with theirs importance in assembling the final image. In the specific case of wavelet coding, lower order coefficients, representing low frequency data, are prioritized into lower-valued ordinal layers, such as layer 1, layer 2, or the like, while higher frequency information (higher order coefficients) representing detail information, are prioritized into higher and higher layers, corresponding to greater and greater amounts of detail.

As was the case with the embodiment of FIG. 4, following transformation and quantization, the various layers are arithmetically coded and entered into an appropriate transmission queue 104 for transmission to a remote location over WAN transmission channels.

In order to retain fidelity with the original image, a lossless portion 102 is provided for containing image data that, when combined with lossy layer information, results in a lossless image. The lossless portion 102 contains data difference information which is constructed by subtracting the original image representation from the assembled image information comprising lossy layers 1 to N−1. This difference data is compressed by a lossless compression technique such as Huffman coding, dynamic Huffman coding, or Lempel-Ziv-Welch coding in order to minimize its particular transmission bandwidth requirements.

As was the case with the lossy layer portion 100, the lossless portion 102 may also be implemented as a plurality of layers, each layer representing perhaps a frequency code, in the case of Huffman coding, or some other statistical weighting in the case of the various other substitutional or statistical compression coding methodologies. Similarly, the lossless information is directed to a respective transmit queue 106, which is flagged as the final queue, i.e., transmitted after all the lossy queues 104 have been streamed out. As was also the case in the embodiment of FIG. 4, after receipt and decoding, the queue contents are summed, in a summing circuit 108 to build a composite image 110.

Figure 7:
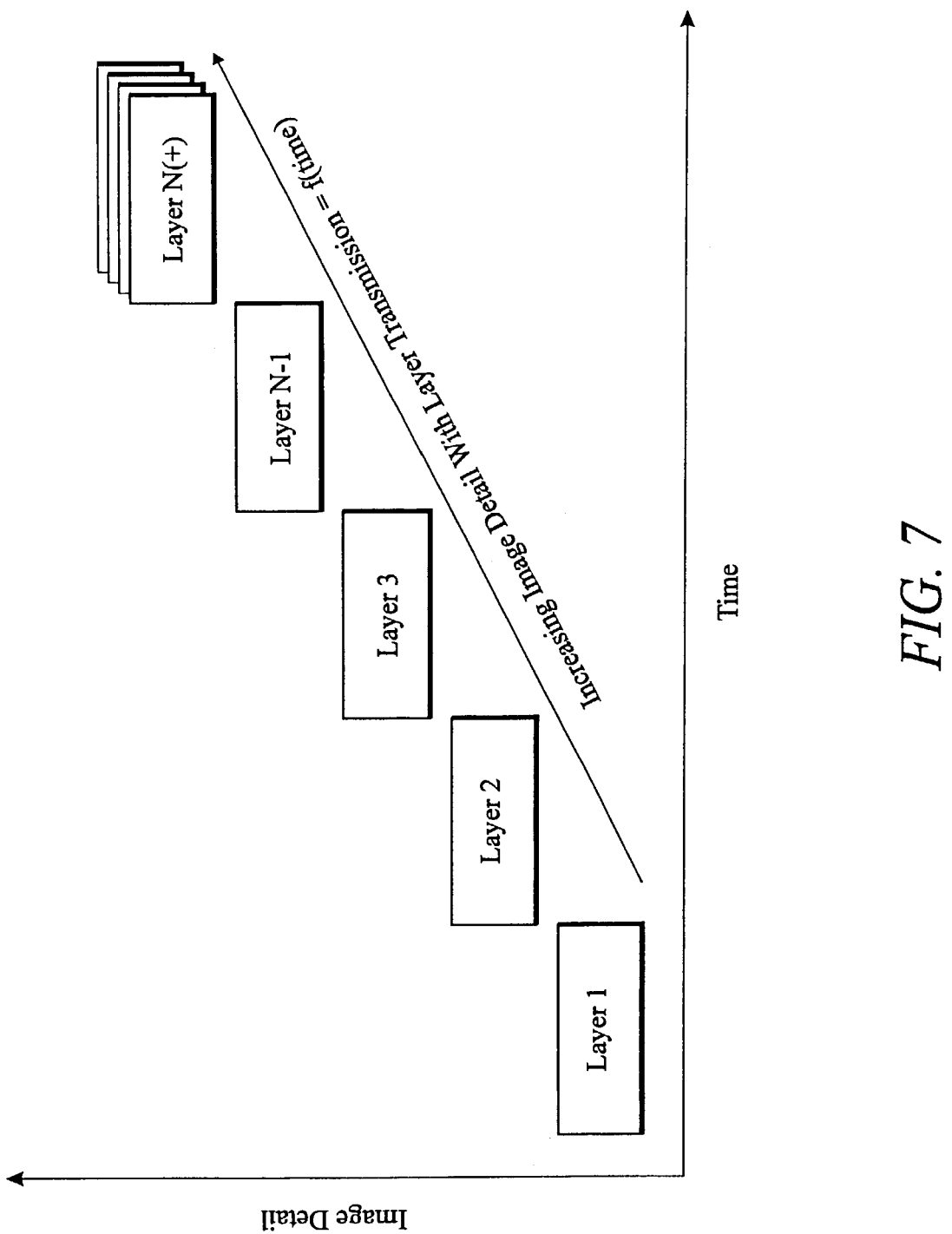
FIG. 7 is a semi-schematic simplified time verses image quality graph depicting the relationship of image detail with viewer perception in accordance with the invention.

As depicted in FIG. 7, the principles of the present invention offer several advantages over lossless or lossy transmission techniques alone. In particular, image sizes processed in accordance with the invention will be expected to be substantially the same as a losslessly compressed image in accordance with LZW or Huffman statistical coding, while retaining the rapid download and viewing capability of a lossy compression technique such as JPEG. The present invention realizes these advantages by the particular nature of its transmission queueing which provides the ability to stream an image to remote locations at a high data rate with an attendant reduction in image detail for rapid viewing, while filling-in image detail with time. Thus, the present invention is able to deliver an image at a level of detail proportional to a visual perception level of a user. In the case of a large image, such as a pathology slide, as a user scans the specimen, image information is accessed from the higher priority transmission queues, i.e., those queues containing only lower frequency (lower detail) information. Transmission queue sequencing can be understood as being related to stage motion or frame translation, with transmission queueing recycling to higher priorities as the image translates. "Fast panning" across an image only allows higher priority queues to be transmitted and downloaded. As image translation speed is reduced, more and more transmission queues are accessed thereby adding detail to the displayed image. When an area of interest is identified, and frame translation ceases, all layers queued for transmission are downloaded giving a resulting image substantially the same as the original optically obtained image.

It should be understood from the time graph of FIG. 7, that the lower ordinal layers (higher priority layers) have already been downloaded as a function of frame translation. Thus, as an image ceases to move, only the higher ordinal layers (lower priority queues) and the lossless layers need be transmitted in order to reconstruct the final image. Thus, a clinician may rapidly traverse an image, looking at only the lower detail levels, and perceiving a near visually lossless image. As translation slows down, greater and greater amounts of detail are allowed to fill in as additional transmission queues, containing additional detail layers, are accessed. Image detail, then, becomes a cumulative time function, with transmission bandwidth requirements remaining substantially level over time. The final image is thus the result of a time integration, with the full-size image being constructed "vertically" by "overlaying", or enriching, detail information onto a low resolution primitive, as opposed to the entire image's being captured, compressed, transmitted and "painted" on a display.

When applied to an application such as pathology slide evaluation, principles of the present invention might be used in combination with an image "tiling" or mosaic creation technique such as described previously. In this particular exemplary embodiment, very large images are segmented into a mosaic of tiles, i.e., a 16×16 pattern, for example, each of which are processed in accordance with the transform, quantization, coding and queueing methodology of the invention. Specifically, compression might be lossless, lossy or the particular combination of the two described above in order to minimize bandwidth utilization and improve download and viewing speed. The lossless/lossy transmission methodology described above, is particularly useful in this particular application. When a large, overall image is being initially constructed, it is only necessary to create the mosaic tiles with an intermediate degree of detail, since a user's perceptual ability cannot discern fine structure at such low magnifications. Thus, each tile's image information need only be processed by the lossy techniques described above and only the higher priority transmission queues (lower frequency data) need be transmitted.

An image mosiac constructed in such fashion might then support image detail sufficient to represent 2×, 5× and even 10× magnifications, such that rapid identification of areas of interest in the slide might be made at lower magnification levels, while fine structure for those areas of interest remain untransmitted until such time as a user requires the additional image information.

In this particular instance, image detail delivery is again proportional to a user's perception level, but rather than being an function of frame translation speed, it is a function of magnification level. At low magnifications (the entire image for example) sufficient detail for user perception is provided by the lossy compressed data contained in the higher priority transmission queues. There is no need to provide fine structure in such circumstances, because the user is unable to provide it. Bandwidth is thereby conserved. As magnification increases, image size necessarily decreases. Accordingly, fine structure detail need only be provided for a small portion of an image at any particular time. Thus, fine structure detail is not required for the entire image, again conserving transmission bandwidth while not degrading the image.

A further advantage of the present invention can be understood when it is realized that it need not be limited to transmitting real-time videographic images captured over a telemicroscopy system. Specifically, the system and method of the present invention has equal utility in transmitting and viewing "virtual specimen" videographic information which has been previously captured by a computer controlled telemicroscope and which has been stored in a server database as a sequence of high-resolution images. When the digital nature of information captured by a telemicroscope's video camera is considered, it will be understood that this information can be used to define a multi-dimensional mosaic of a sample specimen which may be "navigated" in precisely the same fashion as an actual sample. Virtual specimens can be evaluated in detail by traversing the video file's virtual dimensions in a manner quite similar to issuing X, Y and Z motion commands to a telemicroscope. When it is understood that the systems described are easily capable of incorporating real-time video conferencing applications suitable for connection to the described telecommunications interfaces, one having skill in the art will immediately appreciate the utility of this system as a means for archiving rare or unusual tissue samples, either for further review or future comparison purposes, consultations and educational presentations.

Although the present invention has been described in connection with a particular illustrated embodiment, it should be understood that various changes, substitutions and alterations can be made without departing from the spirit and scope of the present invention. In particular, the novel system has been described in connection with a telemicroscopy apparatus that incorporates a conventional optical microscope. It should be realized that future instruments adapted to image microscopic specimens may not be configured as microscopes in the traditional sense but function rather more like desktop scanners having compound optical systems. Digital signals representing a microscopic image might not conform to the NTSC standard nor even be video signals as that term is currently contemplated. It should be understood by those having skill in the art that the form and arrangement of digital signals representing a microscopic image is not the primary concern of the invention, but rather represents an information package which is operated on by a novel compression system and method.

There has now been brought to the field of telemicroscopy an improved system and method for compression packaging video image data in a manner which overcomes channel capacity limitations and allows almost real-time evaluation of tissue samples. A flexible, variable and self-adapting methodology is used to compress and reduce the image datastream according to the observation activity of a user.

The invention claimed is:

1. A method for compressing visual image data for transmission over a bandwidth restricted transmission channel, comprising:

compressing visual image data indicative of an image by decomposing the image data into a plurality of resolution metric associated components, each respective resolution metric defining an image resolution level;

packetizing each of the resolution metric associated components into respective ones of a plurality of transmission protocol specific packets;

storing said plurality of transmission protocol specific packets in priority queues, where each priority queue has a discrete transmission priority ranging from highest to lowest priority;

adaptively directing each of the transmission protocol specific packets to a respective priority queue, wherein transmission packets are directed to priority queues having transmission priorities in inverse relationship to the image resolution level defined by each resolution metric; and transmitting the contents of the priority queues in accordance with their order of priority.

2. A system for image compression and transmission over bandwidth restricted transmission channels, comprising:

an image compression engine, the image compression engine decomposing an image into a plurality of definition metric associated components, each respective definition metric defining an image resolution level;

a packetization engine for adaptively packaging metric associated components into respective ones of a plurality of transmission protocol specific packets;

a plurality of priority queues, each priority queue receiving and storing a respective one of the plurality of transmission protocol specific packets, each priority queue having a respective discrete transmission priority ranging from highest to lowest priority, which is in inverse relationship to an image resolution level defined by each metric.

3. A method for compressing visual image data for transmission over a bandwidth restricted transmission channel, comprising:

acquiring visual image data representing an image to be transmitted;

processing the visual image data by:

compressing the image data into a first data set defining a plurality of resolution metric associated component layers in accordance with a lossy compression transform;

summing the resultant image data comprising the layers;

determining a difference data set representing the difference between the resulted image and the acquired image data;

compressing the difference data set into a second data set in accordance with a lossless compression transform;

packetizing each of the data sets into respective ones of a plurality of transmission protocol specific packets;

providing a plurality of priority queues, each priority queue adapted to receive and store a respective one of the plurality of transmission protocol specific packets;

assigning each priority queue a discrete transmission priority ranging from highest to lowest priority; and transmitting the contents of the priority queues in accordance with their order of priority.

4. The method according to claim 3, wherein the resolution metric associated component layers comprising the first data set each define a corresponding image resolution level and wherein transmission packets are directed to priority queues having transmission priorities in inverse relationship to the image resolution level defined by each resolution metric.

5. A system for layered image compression and transmission over bandwidth restricted transmission channels, comprising:

a frame differencing engine adapted to compare a present frame of a visual image data characterized by frame translations at variable time rates of change to a previous frame to thereby extract newly added image information;

an image compression engine, the compression engine decomposing the newly added image information into a plurality of definition metric associated components, each respective definition metric defining a progressive image resolution level;

a packetization engine adaptively packaging metric associated components into respective ones of a plurality of transmission protocol specific packets;

a plurality of priority queues, each priority queue receiving and storing a respective one of the plurality of transmission protocol specific packets, each priority queue having a respective discrete transmission priority progressing from highest to lowest priority; and an assigning structure which assigns transmission packets containing metric associated components a priority queue having a priority in inverse relationship to the progressive image resolution level defined by each metric.

6. A method for compressing visual image data for transmission over a bandwidth restricted transmission channel, comprising:

acquiring visual image data representing an image to be transmitted;

compressing the visual image data by decomposing the image data into a plurality of resolution metric associated components, each respective resolution metric defining image data at a particular image resolution level;

packetizing each of the resolution metric associated components into respective ones of a plurality of transmission protocol specific packets;

adaptively directing and storing each of the transmission protocol specific packets to a respective priority queues where each priority queue having a transmission priority and adapted to receive and store a respective one of the plurality of transmission protocol specific packets in the plurality; and transmitting the contents of the priority queues over the bandwidth restricted transmission channel in accordance with their order of priority.

7. A system for image compression and transmission over bandwidth restricted transmission channel, said system comprising:

a telemicroscopy system for acquiring visual image data representing an image to be transmitted;

an image compression engine, the image compression engine receiving said visual image data and decomposing the image data into a plurality of resolution metric associated components, each respective resolution metric defining image data at a particular image resolution level;

a packetizing engine for adaptively packaging the resolution metric associated components into respective ones of a plurality of transmission protocol specific packets;

a plurality of priority queues, each priority queue having a transmission priority and adapted to receive and store a respective one of the plurality of transmission protocol specific packets; and a transmitter that transmits the contents of the priority queues over the bandwidth restricted transmission channel in order of priority.

8. A method for compressing visual image data for transmission over a bandwidth restricted transmission channel, comprising:

acquiring visual image data representing an image to be transmitted;

compressing the image data into a first data set having a plurality of resolution metric associated component layers, each resolution metric associated component layer defining image data at a corresponding image resolution level;

summing the resultant image data comprising the layers into resultant image data;

determining a difference data representing the difference between the resultant image data and the acquired image data; and compressing the difference data set into a second data set in accordance with a lossless compression transform;

packetizing each of the data sets into respective ones of a plurality of transmission protocol specific packets;

providing a plurality of priority queues, each priority queue having an assigned transmission priority and adapted to receive and store a respective one of the plurality of transmission protocol specific packets;

assigning and storing each of the plurality of transmission protocol specific packets to one of the plurality of priority queues; and transmitting the contents of the priority queues in accordance with their assigned transmission priority.

9. The method according to claim 8, wherein the assigning and storing each of the plurality of transmission protocol specific packets to one of the plurality of priority queues assigns and stores transmission packets to priority queues having transmission priorities in an inverse relationship to the image resolution level defined by the resolution metric contained within the packet.

10. A system for layered image compression and transmission over bandwidth restricted transmission channels, comprising:

a telemicroscopy system acquiring visual image data representing an image to be transmitted, the visual image data characterized by frame translations at variable time rates of change;

a frame differencing engine adapted to compare a present frame to a previous frame to thereby extract newly added image information;

an image compression engine, the compression engine decomposing the newly added image information into a plurality of definition metric associated components, each respective definition metric defining a progressive image resolution level;

a packetization engine for adaptively packaging the definition metric associated components into respective ones of a plurality of transmission protocol specific packets;

a plurality of priority queues, each priority queue receiving and storing a respective one of the plurality of transmission protocol specific packets, each priority queue having a respective discrete transmission priority progressing from highest to lowest; and a transmission queue assignment part, assigning transmission packets containing metric associated components to a priority queue having a priority in inverse relationship to the progressive image resolution level defined by each metric.

11. The method of claim 6, wherein the step of adaptively directing and storing each of the transmission protocol specific packets to a respective one of the priority queues in the plurality; directs and stores the transmission protocol specific packets to priority queues having transmission priorities in an inverse relationship to the image resolution level defined by the resolution metric contained in the respective transmission protocol specific packet.

12. The system of claim 7, wherein the plurality of priority queues receive and store the plurality of transmission protocol specific packets in reverse order of the image resolution level defined by the resolution metric contained in each packet such that priority queues having higher transmission priority receive and store packets having resolution metrics which define a lower image resolution level and priority queues having lower transmission priority receive and store packets having resolution metrics which define a higher image resolution level.

13. A method for providing a series of images of a sample comprising:

providing the sample on a sample stage, the sample stage defining a planar surface moveable to a three dimensional position;

adjusting the stage to a first position and capturing first image data of the sample at a first resolution such that the first image data covers a first portion of the sample;

compressing and packetizing the first image data and transmitting the compressed and packetized first image data over a bandwidth-restricted transmission channel for storage and display;

adjusting the sample stage to a second position and capturing second image data of the sample at the first resolution such that the second image data covers a second portion of the sample;

comparing the first image data to the second image data in order to determine new image data representing a difference between the first and second image data;

compressing the new image data so it is represented as a set of frequency component coefficients that represent the level of image detail of the new image data, with lower frequency component coefficients representing the least amount of image detail and higher frequency component coefficients representing the highest amount of image detail;

packetizing the frequency component coefficients into a plurality of packets and storing the plurality of packets in a plurality of transmission queues, each transmission queue having an assigned transmission priority level; and selectively transmitting the contents of the transmission queues in order of their priority over the bandwidth restricted transmission channel.

14. The method of claim 13, wherein the packetizing the frequency component coefficients into a plurality of packets and storing the plurality of packets in a plurality of transmission queues stores the packets in the plurality of transmission queues in a reverse order such that priority queues having higher transmission priority levels store packets having lower frequency component coefficients and priority queues having lower transmission priority levels store packets having higher frequency component coefficients.

15. The method of claim 14, wherein in the step of selectively transmitting the contents of the transmission queues in order of their priority, only the contents of transmission queues having higher transmission priority levels are transmitted if the adjustment of the sample stage exceeds a maximum threshold.

16. The method of claim 15, wherein in the step of selectively transmitting the contents of the transmission queues in order of their priority, the contents of transmission queues having lower transmission priority levels are transmitted as the adjustment of the sample stage falls below a maximum threshold.

17. A system for providing a series of images of a sample, the system comprising:

a sample slide defining a planar surface for holding the specimen, said slide stage moveable to a three dimensional position;

an adjustment control mechanism for controlling the lateral movement of the stage in either the lateral X and Y directions, and further controlling the vertical motion of the stage;

an imaging system for capturing image data, wherein the video imaging system:

captures first image data of the sample at a first resolution with the sample stage in first position such that the first image data covers a first portion of the sample; and captures second image data of the sample at the first resolution with the sample stage in different positions such that the second image data covers a second portion of the sample;

comparison module for comparing the first image data to the second image data in order to determine difference image data;

a compression engine for compressing the difference image data so it is represented as a set of frequency component coefficients which represent different levels of image detail of the difference image data, with a lowest frequency component coefficient representing the lowest level of image detail and higher frequency component coefficients representing higher levels of image detail;

packetizing engine for packetizing the frequency component coefficients into a plurality of packets;

a plurality of transmission queues, each transmission queue having an assigned transmission priority level and used for storing the packetized frequency component coefficients; and a transmission means for selectively transmitting the contents of the transmission queues in order of their priority level over the bandwidth restricted transmission channel.

18. The system of claim 17, wherein the packets are stored in the plurality of transmission queues in a reverse order such that priority queues having higher transmission priority levels store packets having lower coefficients and priority queues having lower transmission priority levels store packets having higher coefficients.

19. The system of claim 17, wherein only the contents of the transmission queue having the highest transmission priority level are transmitted if the adjustment of the sample stage a maximum threshold.

20. The system of claim 19, wherein the contents of transmission queues having lower transmission priority levels are transmitted as the adjustment of the sample stage decreases.

21. A moveable slide stage in a telemicroscopy system, said slide stage defining a planar surface for holding a specimen to be analyzed using the telemicroscopy system and comprising:
- a first translational motor control system for controlling motion of the slide stage in first directions lateral to the planar surface;
- a second translational motor control system for controlling motion of the slide stage in a vertical direction, orthogonal to the first directions, such vertical motion occurring at first increments; and
- focus control circuitry including a microstepping motor for further adjusting the slide stage in the vertical direction, such motion occurring at second increments, wherein the second increments are substantially smaller than the first increments, thereby allowing for vertical optical sectioning by providing the micromotions necessary to adequately focus the telemicroscopy system on different image plane levels within the specimen.

22. A system for capturing an image of a specimen, compressing the image and transmitting the image over a bandwidth-restricted transmission channel, said system comprising:
- a telemicroscopy system for capturing visual image data of the specimen, the image data representing an image to be transmitted, the telemicroscopy system including:
  - a moveable slide stage defining a planar surface for holding the specimen, said slide stage having a first translational motor control system for controlling motion for the slide stage in first directions lateral to the planar surface, a second translational motor control system for controlling motion for the slide stage in a vertical direction, orthogonal to the first directions, such vertical motion occurring at first increments, and focus control circuitry including a microstepping motor for further adjusting the slide stage in the vertical direction, such motion occurring at second increments, wherein the second increments are substantially smaller than the first increments, thereby allowing for vertical optical sectioning by providing the micromotions necessary to adequately focus the telemicroscopy system on different image plane levels within the specimen;
- an image compression engine that receives said visual image data and decomposes the image data into a plurality of resolution metric associated components, each resolution metric defining image data at a particular image resolution level; and
- a packetizing engine for adaptively packaging the resolution metric associated components into a plurality of transmission protocol specific packets.

23. The system of claim 22, further comprising:
- a plurality of priority queues, each priority queue having a transmission priority and adapted to receive and store a respective one of the plurality of transmission protocol specific packets; and
- a transmission means coupled to the priority queues for transmitting the contents of the priority queues over the bandwidth restricted transmission channel in order of transmission priority.

24. The system of claim 23, wherein the plurality of priority queues receive and store the plurality of transmission protocol specific packets in reverse order of the image resolution level defined by the resolution metric contained in each packet such that priority queues having higher transmission priority receive and store packets having resolution metrics that define a lower image resolution level and priority queues having lower transmission priority receive and store packets having resolution metrics that define a higher image resolution level.

* * * * *